United States Patent [19]

Vaillancourt

[11] Patent Number: 4,636,313
[45] Date of Patent: Jan. 13, 1987

[54] FLEXIBLE FILTER DISPOSED WITHIN FLEXIBLE CONDUCTOR

[76] Inventor: Vincent L. Vaillancourt, 14 Bunyan Dr., Livingston, N.J. 07039

[21] Appl. No.: 576,864

[22] Filed: Feb. 3, 1984

[51] Int. Cl.$^4$ ............................................. B01D 13/00
[52] U.S. Cl. ................................. 210/436; 210/450; 210/927; 604/126
[58] Field of Search ................. 604/126; 40/927, 459, 40/460, 450, 436, 321.1

[56] References Cited

U.S. PATENT DOCUMENTS

| | | | |
|---|---|---|---|
| 2,681,654 | 6/1954 | Ryan et al. | 604/252 |
| 3,000,504 | 9/1961 | Pfeiffer | 210/448 X |
| 3,834,124 | 9/1974 | Ichikawa | 210/927 X |
| 4,004,587 | 1/1977 | Jess | 210/927 X |
| 4,066,556 | 1/1978 | Vaillancourt | 210/927 X |
| 4,276,170 | 6/1981 | Vaillancourt | 210/448 X |
| 4,306,973 | 12/1981 | Ishikawa | 604/406 X |
| 4,318,812 | 3/1982 | Vcelka | 210/927 X |

*Primary Examiner*—Frank Spear
*Attorney, Agent, or Firm*—Ralph R. Roberts

[57] ABSTRACT

There is shown and described a tubular flexible filter membrane disposed within a flexible conductor such as IV tubing. This flexible filter membrane is sufficiently smaller in its outer diameter than the inner diameter of the flexible conductor so that a space is provided for the flow of fluid. This flexible filter is hydrophilic and has one end closed to exclude fluid flow to the interior of the filter. The other end of this filter membrane is secured to a tubular conductor and at this secured portion is made non-conductive as to gas and fluid flow through the filter wall. A method of attaching this filter membrane end by heating the thermoplastic filter membrane so as to cause thinning of the wall of the filter membrane and making this thinned portion non-conductive as to gas flow is shown. Potting, using polyurethane compounds, may be used but is time-consuming and costly. The flexible conductive tubing is usually produced by extruding dies and methods so ribs and/or flutes may be formed and are contemplated although not illustrated. Heating of the end of the filter membrane is shown by two modes of apparatus. When this filter design is used in conjunction with a drainage system, a vent as well as anti-reflux devices are not required in the collection bag.

22 Claims, 21 Drawing Figures

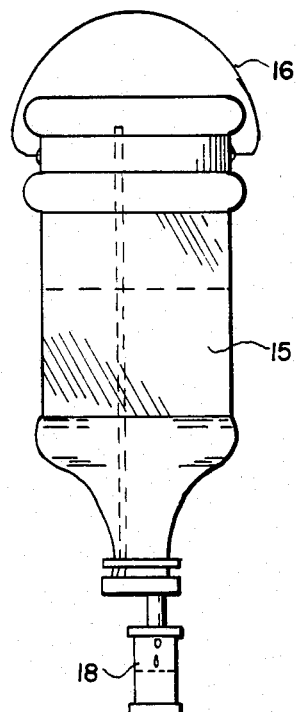
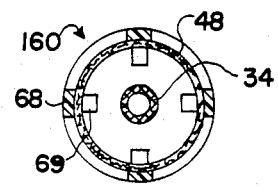
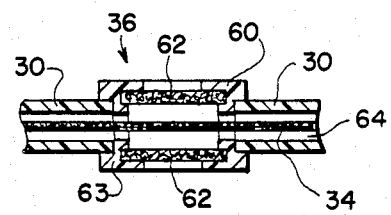
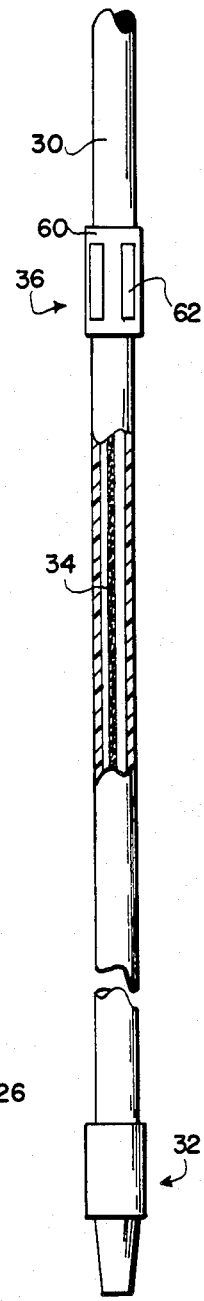
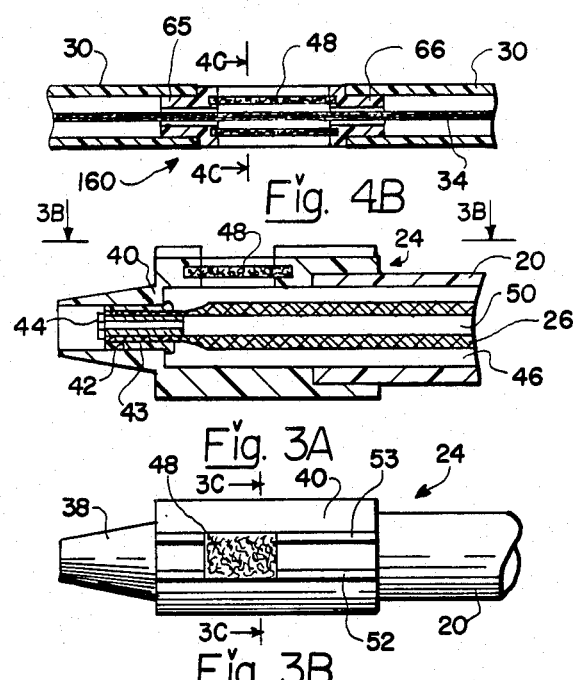
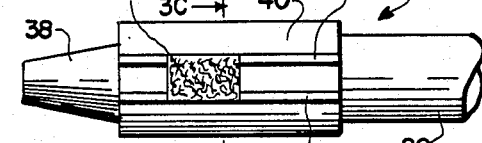
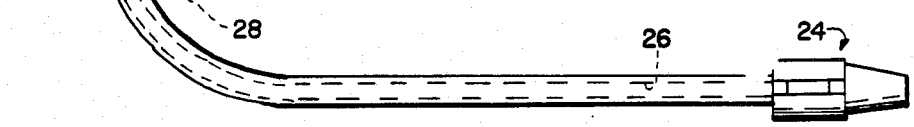

FLEXIBLE FILTER DISPOSED WITHIN FLEXIBLE CONDUCTOR

BACKGROUND OF THE INVENTION

1. Field of the Invention

With reference to the classification of art as established in and by the United States Patent and Trademark Office this invention pertains to filter devices usually concerned with surgical procedures or with drainage devices used by people. The general class may be in "Surgery" or may be in "Liquid Purification or Separation". The filter means hereafter shown and described pertains to flexible tubular filters disposed within and spaced from the interior sidewalls of a tubular flexible conductor.

2. Description of the Prior Art

A search of the art revealed many filters disposed within flexible, impervious outer membranes. Of particular note is U.S. Pat. No. 3,506,130 as issued on Apr. 14, 1970 to SHAYE. This SHAYE embodiment requires manual venting and in this filter chamber a filter body is a substantially flat membrane and not Applicant's tubular membrane hereinafter described. U.S. Pat. No. 3,854,907 as issued Dec. 17, 1974 to RISING includes a housing and a filter membrane. The housing of RISING is rigid and the filter membrane is not a flexible member. In this instant invention the flexible filter is tubular and is disposed within a flexible tubular member such as I.V. tubing. U.S. Pat. No. 4,276,170 as issued June 30, 1981 to the Applicant shows a filter membrane in flat form in a housing. Construction of the filter is particularly shown in FIGS. 4, 5, 6 and 7. Also of note is U.S. Pat. No. 4,341,538 as issued July 27, 1982 to VADNAY et al. This is an I.V. filter in which the membrane is disposed at an angle within the chamber which is rigid. A low profile inline filter is shown in U.S. Pat. No. 4,400,277 as issued Aug. 23, 1983 to LEASON. This inline filter anticipates substantially rigid support of the tubular filter.

The filter system of this invention to be hereinafter more fully described contemplates a tubular filter membrane usually extruded and having the capability of excluding bacteria and the like. Conventionally this filter is used with tubing of rather small diameter such as I.V. conventionally sized or drainage tubing. The filter membrane is usually of plastic and through the process to be described is secured to a molded connecting device including luer lock connectors to I.V. tubing.

The present invention is mainly directed to a filter assembly providing a unique structure particularly useful in the filtering of parenteral fluids during the administration of such fluids. The manufacture of the assembly components provides a novel filter structure. In and with I.V. administration procedures the solution is usually filtered then proceeds through an extension set to a catheter to administration to the patient. The filter membrane is sized to remove bacteria and other contaminants that may be in the solution.

For the most part, the commercially known I.V. filters utilize a hard-rigid casing or envelope to provide the required strength and protection and to prevent unwanted and accidental damage to the filter. This is a significant limitation since patients having such filter units taped to their anatomy develop pressure sores should they lie on these filters for any significant period of time. Attempts have been made to develop flexible filters to overcome this drawback. A problem encountered with such flexible filters used with I.V. administration is that after a flow control clamp is closed (this clamp is positioned above the filter), after priming or filling the system, the fluid continues to flow because of the encasement housing of said filter. Where a flexible housing is used, the atmospheric pressure causes a collapse of the housing, resulting in a continued fluid flow or dribble. This continued flow or dribble causes spillage, loss of priming volume and a ready source of and for site contamination. Most importantly, this dribble breaks the sterile technique supplied by the present invention. A flow control valve or clamp when placed below the filter is not desirable for two prime reasons. First, it is desirable that the filter be placed as close to a patient or recipient as possible, and, second, a flow control device requires a rigid member(s) which is outside of the IV tubing and not only provides bulk, but also pressure points or areas which often irritate the skin of the patient when he or she accidentally rolls on top of the device. This is especially true of older or debilitated patients. The present invention does not present such problems.

Except for large rigid IV filters which utilize half their area to provide air venting, all IV filters are position sensitive. The present invention provides air venting regardless of position, and the air vent is made small in size and does not protrude to make an uncomfortable addition. Two means are presented for providing this air vent and both provide a hydrophobic membrane which acts as a barrier to bacteria and the like while passing air. The flexible filter of this invention is tubular in form and is small enough to be inserted and disposed within the flexible IV tubing. This IV tubing is characterized as being flexible and capable of being formed into a five-eighths inch ($\frac{5}{8}''$) bend radius or larger without collapsing and has sufficient wall thickness. to prevent collapse when the tubing is empty. With the present invention, the flow control valve or clamp when shut off above the filter instantly stops fluid flow. Fluid is retained within the flexible filter housing and priming volume is maintained. With the present invention, dribble does not occur and is not present.

SUMMARY OF THE INVENTION

This invention may be summarized at least in part with reference to its objects.

It is an object of this invention to provide, and it does provide, an IV conducting tubing of flexible construction and with an internal/tubular flexible filter membrane providing an external and internal path within the tubing and with the filter providing bacteria retentive filtration. (In this specification, "Bacteria Retentive" is defined as the filter product having a Log Reduction Value of 5 or greater.) This filter is hydrophilic and this filtration may be accomplished without the use of pumps or other mechanical assists. This filter assembly may be taped to a patient's anatomy without any fear that pressure points will be generated. The filter assembly is position insensitive with the filter positioned in any convenient way on the patient's anatomy. The location of the air filter assures that entrapped air will be vented before shutdown of the fluid filter can occur.

It is a further object of this invention to provide, and it does, a flexible filter assembly for use in and with a length of IV tubing, this flexible filter is of a tubular configuration and hydrophilic with bacteria retentive filtering capability. This IV tubing is made with a hydrophobic membrane secured to a filter retaining end member and disposed so as to be position insensitive.

In brief, this invention provides a filter assembly which utilizes an administration set and particularly the IV tubing used therewith. Within this flexible IV tubing is placed a second filter tube of hollow fiber construction which is bacteria retentive. This filter tube is pinched off or closed at one end and secured to an adapter at the other. Usually this connector is of the luer type. An in-line hydrophobic bacteria retentive filter is positioned near an end of the hollow fiber filter to provide a vent for air within the IV tubing. This construction, to be hereinafter more fully shown and described, adds no bulk or restrictive geometry to the administrative set or use. The only added parts are the internal filter and vent, and these do not significantly add to the external size of the set.

The method of securing the membrane hollow fiber to a fitting-ferrule is believed to be unique. It has been found that by heating the hollow fiber tubing above its transition termperature, the tubing loses upward of 50% of its wall thickness at this heated area with almost no shrinkage (reduction in diameter) at its inner tubular diameter. This is not found in heat shrink tubing which is used where the inner diameter and outer diameter shrink considerably and concurrently the wall thickness *increases* significantly.

This heating of the tubular filter provides a means of solidifying the wall and is therefore not to be confused with commercially used heat shrink materials. The internal diameter reduction of the tubular filter is quite small in comparison to the shrinkage of the wall of said tubular filter. However, when the internal ferrule is sized so that it is just slightly smaller (0.001 to 0.005/one thousand to five thousandths of an inch) than the unheated tubular filter's inner diameter the combination of shrinkage and wall reduction of the tubing resulting with said heating of the hollow fiber membrane tubing provides a secure fluid, and most importantly an air tight mechanical seal between the ferrule and tubular filter. This connection can be made to withstand high pressures by simply reinforcing the reduced tubing section with a collar, shrink band swaged connector or other means which will reinforce the hollow membrane tubing reduced section.

It is to be noted that this reduced section unlike the rest of the hollow fiber membrane is tough, has excellent strength properties, (non-brittle), and is essentially free from pores thereby preventing air from going around or through this section of the hollow fiber tubing. Since air cannot go through this reduced section this allows the finished filter to be bubble point tested for product integrity, a very useful test and criteria for product performance acceptance. The tubular filter is of polypropylene but this method can also be used with polysulfone hollow fiber membranes. Only different temperatures are required to reduce the tubing section to provide the desired method of mounting to a fitting-ferrule.

In another embodiment, the filter of this invention provides for filtering within a drain tube which is connected to a collector bag such as for urine and particularly for use in a hospital This filter prevents bacteria that develop within the drain bag from ascending the drain line and thence into the catheter and ultimately into the patient's bladder causing UTI (urinary tract infection). The apparatus to be hereinafter disclosed also eontemplates and provides a means for allowing the drain bag to be disconnected from the drain line without concern for invasion of the drain line by bacteria from the surrounding environment (urine in the bag) or from bacteria in the atmosphere. This apparatus allows the hospital personnel to remove the collection bag once it is filled and dispose of the filled bag without having to empty the bag. A new disposable bag (sterile or non-sterile) may be hooked up to replace the discarded bag. This reconnection may be and is easily achieved and in a convenient manner. This embodiment provides a "true closed system" since as and when the collector-drainage bag is disconnected the drain lumen is permanently sealed from bacteria in the environment passing upstream through the bacteria filter.

The following embodiments provide many advantages of the known filter products. Among these advantages are:

No Pressure Points—A major problem associated with current IV Filter products is their rigidity and bulk. As a consequence of these factors, general nursing practice is to keep the IV Filters away from the patient or when in proximity to the patient they contain extension sets and are taped to the patient's anatomy remote from the venipuncture area. This prevents the development of pressure sores and ulcers (skin). This product being contained within the tubing does not suffer from such a problem. The filter can be positioned on the patient's anatomy with no regard to this potential problem, hence it can easily be very close to the venipuncture site (in fact it can terminate at the venipuncture catheter's hub.)

Flexible—The IV Filter is as flexible as the IV administration set tubing. The product can easily be looped (turned back on itself) without malfunction.

No Hold up—With other filters we speak of hold-up, that is, the amount of fluid that is required to fill up the IV Filter system. Since this product is an integral part of the IV Administration Set tubing there really isn't any hold-up.

High Pressure System—Whereas in other IV Filter systems the filter members are considered to be the weak point as to how much pressure an IV system can withstand when a pump is used in this system, using the filter of this invention, the system is as strong as the administration set tubing (generally greater than 100 psi).

Continuing Flow—Up to now all flexible systems have suffered from their inability to discontinue flowing when shutoff upstream from the filter. After priming the system to remove all air, it is standard practice to shut off the flow of fluid upstream from the filter where the flow control clamp is located. Previous IV flexible filters begin to collapse after shut-off forcing fluid out of the distal end of the IV administration Set. This makes it impossible for the nurse to set the IV administration set aside until the venipuncture is completed. (This is existing practice). The product of this invention overcomes that problem since the natural tendency of the tube is to retain its shape. It actually requires an external pressure (such as squeezing) after priming and clamp shut off to get any fluid out of the distal end. Thus, this invention overcomes a major disadvantage of all previous IV flexible filter sets.

Universal Air Vent—It has been found that entrapped air in this design is pushed to the air vent. In other words, the air actually seeks the vent in this design. It is virtually impossible for this product to become air bound due to the invention design and geometry.

In addition to the above summary, the following disclosure is detailed to insure adequacy and aid in understanding of the invention. This disclosure, however, is not intended to cover each new inventive concept no matter how it may later be disguised by variations in form or additions of further improvements. For this reason, there have been chosen specific embodiments of a flexible tubular filter disposed with a flexible conductor as adopted for use particularly in administration sets (IV) and in showing a preferred means for securing said filter to a connector. These specific embodiments have been chosen for the purposes of illustration and description as shown in the accompanying drawing(s) wherein:

BRIEF DESCRIPTION OF THE DRAWINGS

FIG. 1 represents a side view, partly diagrammatic, with a portion of the tubing extension absent, this view showing an IV bottle in discharge condition with a connected drip chamber, tubing, shut-off to flow-control, clamp and a flexible filter within this IV tubing and a vented connector end member;

FIG. 2 represents a side view, partly diagrammatic and partly in section, and showing a length of IV tubing in which the filter is tubular and a vent means is provided in the intermediate length of tubing;

FIG. 3 B is a plan view of the connector of FIG. 3 A, this view taken on the line 3 B—3 B and looking in the direction of the arrows;

FIG. 3 C represents a sectional view taken on the line 3 C—3 C of FIG. 3 B and looking in the direction of the arrows:

FIG. 4 A represents in a side sectional view and in enlarged scale the intermediate filter vent provided in the intermediate portion of the IV tubing of FIG. 2;

FIG. 4 B represents in a side sectional view an alternate construction of an intermediate filter vent similar to than of FIG. 4 A but with the housing slightly reduced in diameter for use with IV tubing;

FIG. 4 C represents a sectional view, diagrammatic, and taken on the line 4 C—4 C of FIG. 4 B and looking in the direction of the arrows;

FIG. 6 B represents the sectional view of FIG. 6 A but with the tubular filter now heat set to the metal ferrule;

FIG. 6 C represents a side view, partly diagrammatic and partly in section, and showing a rubber-like tubular outer member prior to positioning on the end of the tubular filter;

FIG. 6 D represents a side view, partly diagrammatic, and partly in section and showing the rubber-like tubular member now positioned as a sleeve on the end of the secured tubular filter;

FIG. 8 B represents a fragmentary sectional side view in an enlarged scale of the closing of the end of the tubular filter as carried within IV tubing, and;

In the following description and in the claims, various details are indentified by specific names for convenience. These names are intended to be generic in their application. Corresponding reference characters refer to like members throughout the several figures of the drawings.

EMBODIMENT OF FIG. 1

Figure 9A:
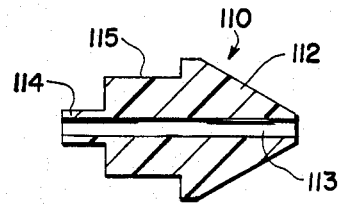
FIGS. 9 A, 9 B, 9 C, 9 D, and 9 E represent sectional side views, partly diagrammatic, and showing a progressive assembly of a tubular filter to a vented molded connector end. The sleeve for this connector end provides the vent.

Referring now to the drawings, there is depicted a typical IV hook-up of a container 15 to which a hanger 16 is attached and is used in the usual manner. A drip chamber 18 is flow-connected to IV tubing 20 which usually includes a flow-control clamp 22. Downstream of the clamp 22, the IV tubing 20 continues to a connector 24, to be more fully described in connection with FIGS. 3 A and 3 B. A tubular filter 26 is secured to the connector 24 and is closed by being heat-sealed to itself or by a plug 28 or the like at a determined distance upstream from connector 24.

EMBODIMENT OF FIG. 2

In FIG. 2 a length of IV tubing 30 is shown with a connector 32 which carries and secures therein a flexible tubular filter member 34. This tubular filter 34 is surrounded by a vent filter member 36 as shown in detail in FIG. 4 A or FIG. 4 B. The connector 32 is very similar to that shown in detail in FIGS. 9 A through 9 D but has no vent since venting is provided in the IV tubing. It is of note that this tubing member as is shown in FIG. 2 occupies little more physical protrusion and diameters than that of conventional IV tubing. This vent is shown in detail in FIG. 4 A.

Figure 3C:
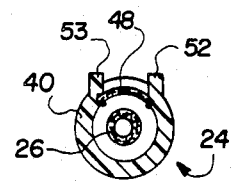
FIG. 3 A represents in a side sectional view and in enlarged scale the connector end of FIG. 1 showing the vent means provided in this connector.
Figure 9B:
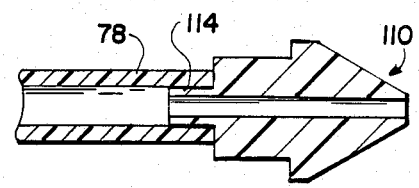
Figure 9C:
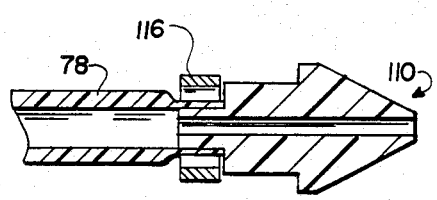
Figure 9E:
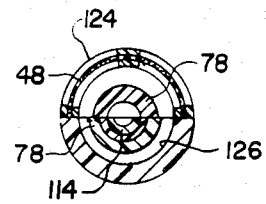
Figure 9D:
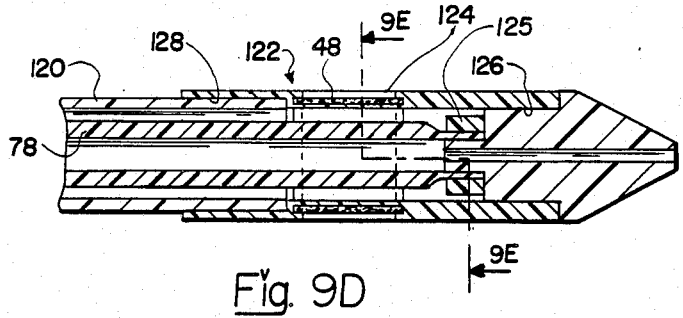

EMBODIMENT OF FIG. 3 A, 3 B, and 3C

The connector 24 conventionally has a tapered extending end portion 38 which is shown as an integral portion of a molded end member generally identified as 40. This member 40 has a bore 42 sized and adapted to retain in a fluid-tight manner a shouldered bushing 43. The tubular filter 26 is tightly secured to a ferrule 44. The tubing 20 is secured to the connector member 40, usually by solvent sealing, but cement may be employed. To provide for the escape of air in the tubular passageway 46, there is provided a hydrophobic filter 48 which is of sufficient area to pass any air that may proceed from the drip chamber 18 toward the connector 24.

The IV tubing 20 carries the fluid from the drip chamber 18 to and through the flow-control clamp 22 which is adjusted to shut off or determine the rate of flow of the fluid. This delivered fluid is now brought in way of and surrounds the tubular filter membrane 26. This filter membrane 26 is a hollow tubular member and in a delivery system to human patients provides bacteria filtration by having an LRV of five. The upstream end is closed at 28 by a pinch-off or like closing means. Fluid passes into the interior passageway 50 of this filter and thence through the ferrule 44 to other devices such as a catheter.

The connector member 40 is generally tubular in configuration but, as shown in FIGS. 3 B and 3 C, the molded connector member 40 has protruding rib portions 52 and 53 providing an air pathway therebetween for air or gases from the interior passageway 46, thence through membrane 48 and to the atmosphere. This securing of membrane 48 enables escaping air to have four paths of exit if desired. The connector member 40 may be formed to accept a plural number of filter membranes 48. The securing of the filter 26 into the bore 42 contemplates that shouldered bushing 43 is a pressure-tight fit or is slightly resilient so as to secure the filter 26 in a positively sealed and secured condition.

EMBODIMENT OF FIGS. 4 A and 4 B

In FIG. 4 A the IV tubing 30, as depicted in FIG. 2, is shown with a hydrophobic filter providing a vent for air that may develop in the delivery system. As seen in a sectional side view, a vent 36 is formed using a tubular filter sleeve around which is a molding of plastic. This molding retains a plurality of openings for the hydrophobic filter membrane, identified as 62, and is adapted to pass air but to exclude bacteria and the like. The IV tubing 30 is cut transversely and inserted into like recesses to a shoulder 63 formed interior of the molding bore. Solvent sealing, cement, or other securing means may be used to secure and retain the tubing 30 to the molding 60. Tubular passageway 64, between filter 34 and tubing 30, not only carries the delivered fluid but any air developed in the system after the drip chamber 18 and flow control clamp 22, and this air is vented through membranes 62 to preclude "air binding" of the filter 34.

In FIG. 4 B the connector of FIG. 4 A is altered to the extent that the tubular sleeve portion 60 is made so as to protrude less and be substantially the same diameter as the IV tubing 30. As shown, a housing 160 is made as a plastic molding with like shoulders 65 and 66 for the solvent attaching of the ends of tubing 30. Rib portions 68 and 69 are shown in FIG. 4C and are provided so that vents therebetween are present for the passage therethrough of air passing through filter membrane 48. The flexible tubular filter 34 is disposed as in FIG. 4 A. In FIG. 4 C the cross sectional configuration of the sleeve portion of FIG. 4 B is depicted for visual display of this concept.

HEATED DIE AS IN FIGS. 5, 6 A AND 6 B

Figure 5:
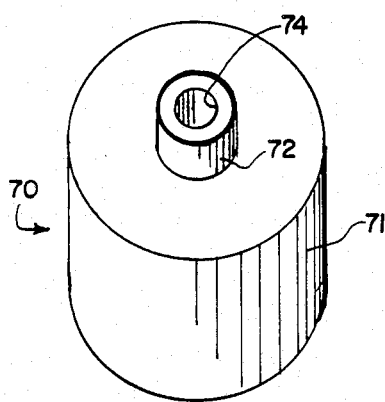
FIG. 5 represents an isometric view, partly diagrammatic, of a heated die by which the tubular filter is heat-set to a metal ferrule.
Figure 6A:
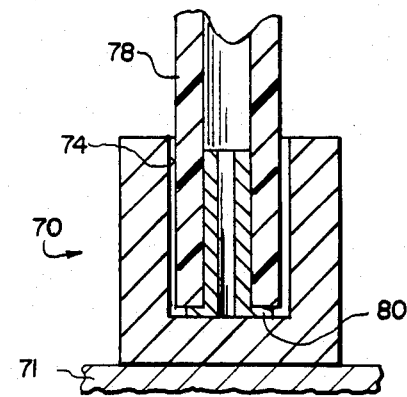
FIG. 6 A represents a sectional side view of the die of FIG. 5, and in a diagrammatic representation and greatly enlarged scale a preliminary step in securing the tubular filter to a metal ferrule.
Figure 6B:
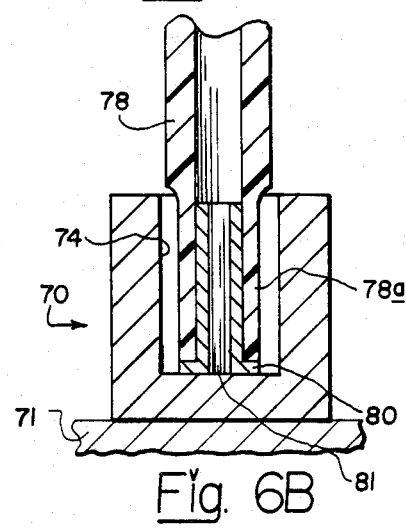
Figure 6C:
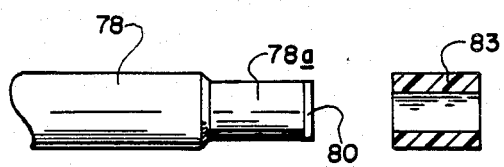
Figure 6D:
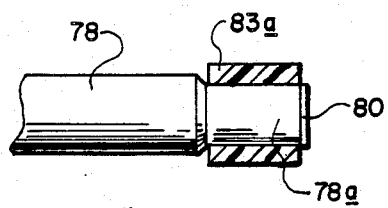

In FIG. 5 is shown a heated die, generally identified as 70, and including a body 71 having a reduced neck portion 72 in which a cylindrical recess 74 is formed. In FIG. 6 A the heated die 70 is indicated in sectional view, and in recess 74 a trimmed end of a plastic filter tubing portion 78 is shown inserted into a shouldered ferrule 80. This ferrule is depicted as metal but may be a high temperature-resistant plastic and having properties such that its size does not change when subjected to the amount of heat in die 70. In FIG. 6 B the arrangement of the tubular end of the filter 78 is shown, but the heat in the die has caused this heated tubing end to reduce in wall thickness. A substantial reduction occurs in the tubing wall 78 a and a small decrease in internal diameter occurs and produces a tight fit around ferrule 80. This reduced wall section not only causes a tight fit of the end of the tubular filter to ferrule 80, but this reduced wall causes this portion to be impervious to fluid flow. This reduction in wall closes off or eliminates the pores in the tubing filter and produces a tubing section of the hollow filter membrane which is hard, tough and sealable to many conventional connectors using known techniques. It is to be noted that ferrule 80 has an internal passageway 81 which provides a continuation of the flow of fluid through the interior of the filter. Although shown with a shoulder at the exit end, this shoulder is not required in this bushing or ferrule. A shoulder does facilitate locating the depth to which the bushing or ferrule is placed within the hollow tubular filter.

EMBODIMENT OF FIGS. 6 C AND 6 D

In FIGS. 6 C and 6 D the end 78 a is shown secured to ferrule 80 and to the right thereof is a resilient tubular member or band 83. This band is usually of plastic or rubber tubing which expands when heated or expanded by appropriate swelling agents. In FIG. 6 D the end 78 a of filter 78 is shown with expanded and now tightly-mounted band, now identified as 83 a, positioned on the end portion 78 a. This shrink fit of band 83 a is conventional but permits tight tolerances to be accommodated and lends itself to automation and assembly.

Figure 7:
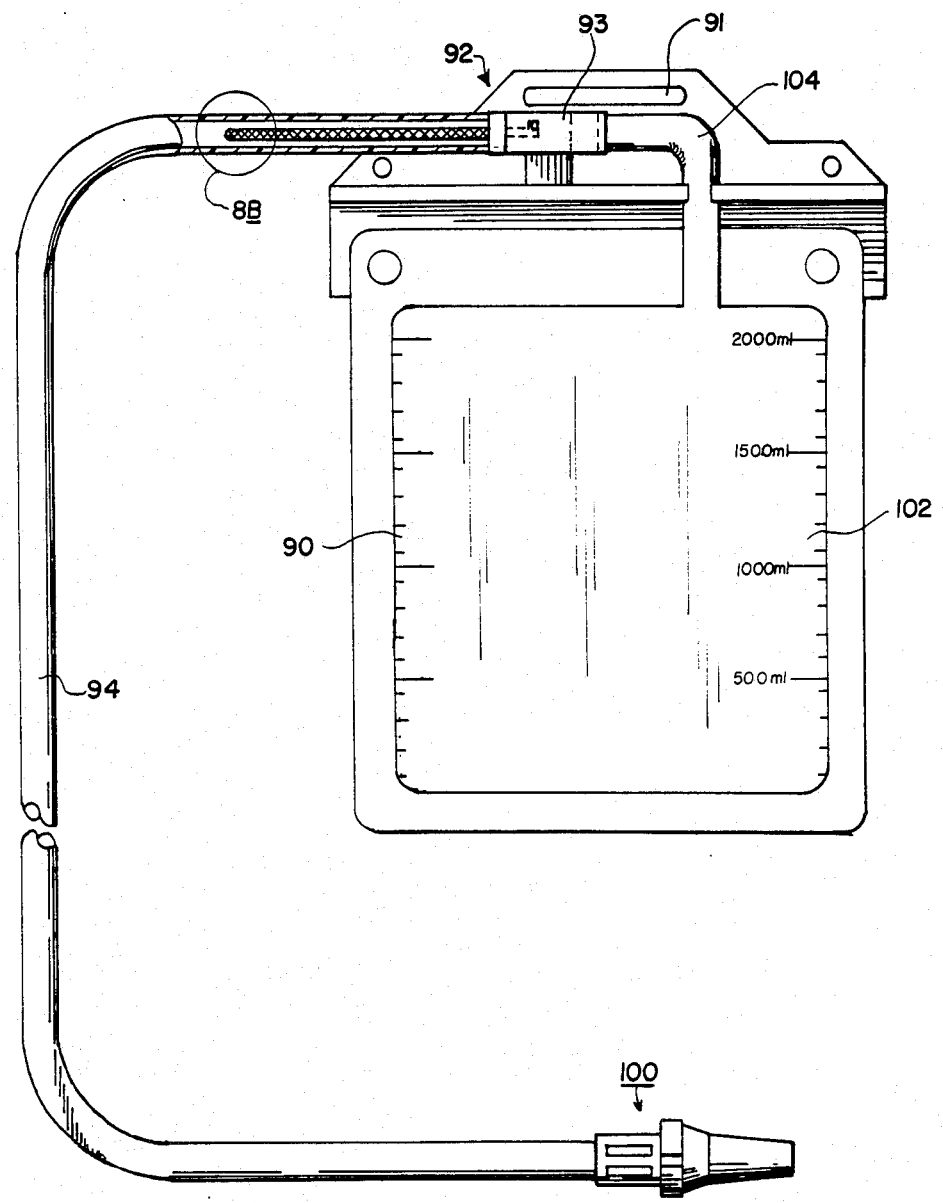
FIG. 7 represents a side view, partly diagrammatic and partly in section, and showing a tubular filter supplied with a removable connector to a collection bag, with the opposite connection end also having a vent so as to eliminate possibility of negative pressure in the patient's abdominal cavity.
Figure 8A:
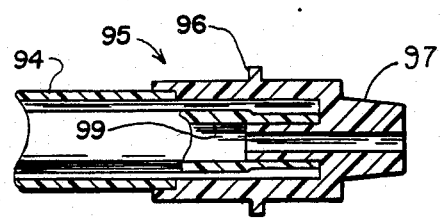
FIG. 8 A represents a side sectional diagrammatic slightly fragmentary, view in a slightly enlarged scale of the removable connector to the bag.
Figure 8B:
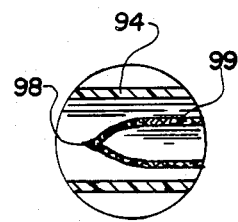

EMBODIMENT OF FIGS. 7, 8 A, 8 B and 8 C

Referring next to the showing of a drain bag arrangement as in FIGS. 7, 8 A, and 8 B and 8 C, the above tubular flexible filter also provides a means for providing a drain bag that may be easily connected to a length of tubing without the potential of bacteria passing through the tubing to the patient. In this showing, a drain bag 90 of flexible plastic sheeting is formed. This bag is not under pressure as this bag is used for drainage from a patient. There is no pressure build-up in this system and vent means for this flexible filter system is generally not required for flow. A hanger 91 is conventionally provided so that the bag may be secured to a bed or the like and with gravity accumulate the discharge from the catheter end. This inlet to the bag is provided with a bayonette fitting generally indicated as 92. A mating connector 93 is attached to a tubing end 104 leading to the interior of bag 90. Connector 92 as shown in FIG. 8 A has tubing 94 secured to a connector 100. As seen in FIG. 8 A, connector 92 is removably mountable in the receiving connector portion 93 of the bag. A hollow filter tube is secured to the connector 92 and is secured to this connector so as to provide a secured filter member. Two opposed pin portions 96 may be formed on connector 92 and conventionally a tapered end 97 is provided on the connector to provide a fluid-tight connection. As depicted in FIG. 8 B, a pinched end 98 of the distal end of a tubular filter 99 provides a closing means for the filter tubing. Means such as a stop plug 28, as in FIG. 1, may also be used. The other end of tubing 94 may be secured to a connector 100 as is usually provided for connection to a drainage catheter in a patient. Connector 100 is conventionally a vented connector to preclude negative pressure in the adominal cavity of the patient to which the catheter is connected.

It is to be noted that bag 90 is indicated printed with indicia 102 indicating (when desired) the amount of discharge from the patient. It is also to be noted that bag 90 is simple and inexpensive in its construction and with the short flexible connector tubing, identified as 104, may or may not be sterile. When filled to the desired amount or for a given period of time, the attendant need only to disconnect 92 from mating connector 93 and the bag, with its contents, may be easily carried and discarded without an inconvenience of using, carrying and washing an open container such as a bed pan or the like. The filter 99 provides a positive cutoff of bacteria that may be produced in the collection bag. The connector 100 provides the connection to the catheter in the patient. This simplified device provides means for the use of a placed catheter for the determined period of time established by the physician without the possibility of ascending bacterial infection from the bag collection due to the opening/closing of the same to the atmosphere. This system is used with bladder pressure at the initial voiding, and gravity with or without bladder pressure thereafter.

EMBODIMENT OF FIGS. 9 A, 9 B, 9 C, 9 D AND 9 E

Next, and finally, there is shown a step-by-step assembly and the components for a connector with a vent sleeve and hydrophobic filter to provide means for the escape of air. As shown in FIG. 9 A, a molding, generally identified as 110, is formed wtih a tapered end 112, a through passageway 113, a small rearwardly-extending, reduced-diameter connection portion 114 and a shoulder portion 115. In FIG. 9 B the flexible tubular filter 78, shown in FIG. 6 A, is mounted on the reduced diameter portion 114. In FIG. 9 C the end of the filter 78 has been heated to cause the reduction as in FIG. 6 B. This heat is supplied by a split heater band (heated by electrical energy) 116 surrounding this reduced section of the tubular filter and provides the amount of heat necessary to reduce the wall thickness of the filter 78 wall. As above noted, this reduction eliminates the pores in the heated wall section of the filter end.

In FIG. 9 D there is shown an end of an IV tubing 120 secured to a sleeve member 122 much like the intermediate connector of FIG. 4 B and 4 C. Exterior rib portions 124 better seen in FIG. 9 E in which are depicted rib portions providing vents through which air may pass through a tubular filter membrane 48. In FIG. 9 D and 9 E there is depicted a retaining band 125 which may be of silicone rubber or other and like rubber member which has been expanded previously to a slip fit over the connector or hollow fiber tube. This band may be of a heat-shrink plastic tube which is heated to set and provide a retaining means of the hollow tubular fiber to the connector. It is to be noted also that the band 125 may be also a crimp fitting of the filter end to the connector. No matter the method, this band provides the securing of the end of the tubular membrane 78 in position. A shoulder 126 secures the end molding 110 in place and solvent, heat sealing, or cement may be used to make the connection fixed and impervious to air or fluid. A shoulder 128 formed at the other end of molding 122 secures the IV tubing to molding 122 by solvent, cement or the like to make this connection fluid-tight and secure.

The above embodiments as shown and described provide a simple but effective process for the securing of a flexible internal tubular filter to a connector housing. This process not only reinforces the filter at the point of the connection, but lends itself to automation and can be programmed for assembly using conventional rotating table-type equipment with automatic feeding and assembly stations.

The above Intravenous IV fluid embodiments contemplate IV tubing in which the flexible tubular filter is disposed for a length of at least two inches. This tubular filter is sufficient smaller than the inner diameter of the IV tubing so as to provide a longitudinally-spaced pathway in which fluid flow is easily achieved. As air or gases may and often develop during IV administration, there is provided a vent for escape of this trapped air or gas. This vent includes a membrane adapted to exclude entry of all particles the size of bacteria and larger.

The vent and connectors are contemplated to be substantially the same diameter or extent as the IV tubing to which they are associated. The desire to maintain small diameters or extents is so that such connectors and/or vents will not cause discomfort or a possible shut-off (kinked tubing) when taping the IV tubing system to the patient. The usual clamp-type shut-off devices are substantially larger than the IV tubing to which they are applied. Accidentally lying on the clamp is uncomfortable, provides pressure points, and on occasions affects use. For this reason, the connectors and vent means of this invention are made so as not to unduly protrude. As shown, the extending portions are about the same extent as the associated IV-type tubing.

The above urinary drain-tube embodiments contemplate the use of conventional size drainage tubing (one-quarter to three-eighths of an inch in diameter). This tubing has a formed bend radius limit before deformation of one and one-half inch to two inches. The flexible tubular filter is disposed for a length of at least six inches within this plastic drainage tubing. Upon initial patient voiding through this drainage system, the filter membrane is wetted, preventing any air or other gases from going into the drainage bag. As a result, the flexible plastic bag only receives fluid (after a small amount of air which is in the tubing line initially and is pushed into the bag as voiding begins) and does not require venting. Existing drainage bags are generally vented due to the build-up of air within the drainage system. Anti-reflux devices, which are a component part of most drainage systems to prevent bacteria migration toward the patient, are not required in the design as illustrated and described above.

The flexible plastic tubing used in these applications is usually produced by extrusion. Internal ribs may be used to promote fluid flow or prevent collapsing. External flutes may be added to provide better gripping or reduce bend radius. Although not illustrated, these designs are contemplated.

Potting, using polyurethane compounds or the like, and the use of hot melt systems, which are the conventional means for sealing hollow fiber tubings, are both avoided in this invention. The major problems associated with these systems include: significant equipment requirements, sophisticated techniques (vacuum to debubble, for example), the clean-up problems they present, and cost.

Terms such as "left," "right," "up," "down," "bottom," "top," "front," "back," "in," "out" and the like are applicable to the embodiments shown and described in conjunction with the drawings. These terms are merely for the purposes of description and do not necessarily apply to the position in which the flexible filter may be constructed or used.

I claim:

1. A body fluid drainage device in which a flexible tubular filter membrane is disposed within a flexible conductor tubing, said conductor tubing capable of being formed into a bend of greater than one and one-half inch radius without collapsing the wall of said flexible tubing and with said tubing having a wall of sufficient thickness and composition so as to prevent collapse when the conductor tubing is empty, this device including:

(a) a length of flexible conductor tubing having a substantially constant configuration;

(b) connector means for securely attaching in a fluid-tight manner a first end of the flexible conductor tubing;

(c) at least a six-inch length of flexible tubular filter membrane in which the filter is bacteria retentive and sized so that the outer diameter of said tubular filter membrane is smaller than the inner diameter of the conductor tubing and with the conductor tubing enclosing said tubular filter membrane, and between this tubular filter and conductor tubing there is sufficient space for fluid flow, said flexible tubular filter membrane being hydrophilic so as to pass fluid absent the passage of air or gas;

(d) a closure means at an interior first end of the flexible tubular filter membrane and configured and disposed to exclude fluid flow from the tubular conductor tubing to the interior of the flexible tubular filter membrane except through the sidewall portion of said filter membrane;

(e) a second connector adapted for releaseable connection in a fluid-tight manner to an inlet of a drainage bag, said connector securely attached to a second end of this flexible tubular filter membrane and providing a fluid flow path from the interior of the flexible tubular filter membrane to said drainage bag;

(f) means for attaching a second end of said flexible conductor tubing to this second connector in a fluid-tight manner with said tubular filter membrane, and the flexible conductor is attached so as to inhibit any fluid flow through transverse portions of the filter membrane at said connecting portion, said tubular membrane preventing a flow of bacteria from the collection bag to that flexible conductor tubing spaced from and surrounding said flexible tubular membrane, and (g) a connector attached to the other end of said flexible conductor tubing, this connector having a vent which includes a hydrophilic filter membrane mounted and secured so that air or gas from the interior of the conductor is excluded except through said vent filter.

2. In an IV delivery system a device in which a flexible tubular filter membrane is disposed within a flexible IV conductor tubing which includes a vent, said conductor tubing capable of being formed into a bend of less than one inch radius without collapsing the wall of said flexible tubing and with said tubing having a wall of sufficient thickness and composition so as to prevent collapse when the conductor tubing is empty, this device including:

(a) a length of flexible conductor tubing having a substantially constant configuration;

(b) a length of flexible tubular filter membrane which is bacteria retentive and sized so that the outer diameter of said tubular filter membrane is smaller than the inner diameter of said IV conductor tubing and with the IV conductor tubing enclosing said tubular filter membrane, and between this tubular filter and IV conductor tubing there is sufficient space for fluid flow, said flexible tubular filter membrane being hydrophilic so as to pass fluid absent the passage of air or gas;

(c) a second filter providing vent means and of hydrophobic material and operatively connected to that space between the flexible tubular filter and the interior of the flexible connector tubing, this second filter and vent means secured in a housing so as to protect this second filter from penetration damage and dislocation, location, this second filter disposed so that air or gas from said space between the IV conductor and the inner flexible filter is required to pass only through said second hydrophobic filter;

(d) a closure means at one end of the flexible tubular filter membrane and configured and disposed to exclude fluid flow from the tubular conductor tubing to the interior of the flexible tubular filter membrane except through the sidewall portion of said filter membrane;

(e) a closure connector at the other end of this flexible tubular filter membrane, this closure connection providing a fluid flow path from the interior of the flexible tubular filter membrane to external means, and (f) a tubular conductor associated with said connector, with said connector having means providing a tubular connecting portion which is tightly connected to said tubular filter membrane and with said connecting portion being attached so as to inhibit any fluid flow through transverse portions of the filter membrane at said connecting portion.

3. A device as in claim 2 in which the connector is provided with locally outwardly extending ribs on the housing which provide air pathways for air to and from the vent filter.

4. A device as in claim 2 in which a vent is provided in an intermediate molding connector and the vent includes a hydrophilic filter membrane being bacteria retentive and which prevents ingress of bacteria to the space for fluid flow.

5. A device as in claim 4 in which the molding is configured so as to provide mounting and securing means for a filter membrane and at the end portions of said molding there is means for securing the ends of flexible conductors of similar or like size.

6. A device as in claim 5 in which the molding includes internal and external ribs by which the vent filter membrane is secured and retained.

7. A device as in claim 2 in which the end connector has a through passageway of a determined size and in this passageway is fixedly mounted an end of the flexible filter membrane, this end attached to a substantially rigid tubular member and at this attached end the flexible filter does not pass fluid or air.

8. A device as in claim 7 in which the tubular member is a tubular ferrule and the attachment is by heating the filter membrane subsequently to cause it to reduce in thickness and tightly surround this ferrule portion.

9. A device as in claim 8 in which the heating is provided by a resistance clamp-type ring device.

10. A device as in claim 8 in which the end of the flexible filter membrane at its reduced thickness is also encased externally by a sleeve member sized to be a snug retaining fit in said passageway and an interference fit on the reduced outer diameter of the flexible tubular filter membrane.

11. A device as in claim 10 in which the connector is formed with an additional tubular shoulder portion formed and sized to receive and retain the flexible conductor and this tubular shoulder portion provided with the vent means whereby air exterior of the filter tubing membrane passes through said vent means.

12. A device as in claim 11 in which the vent means is a hydrophobic filter membrane.

13. A device as in claim 10 in which the ferrule is of metal and the heating of the end of the flexible tubular filter membrane is by a heated die.

14. A device as in claim 13 in which the outer sleeve member is of silicone rubber.

15. A device as in claim 13 in which the outer sleeve member is of a ring-like member of shrink tubing.

16. A device, as in claim 2, in which the tubular membrane, after connection, is at least two inches in length.

17. A body fluid drainage device in which a flexible tubular filter membrane is disposed within a flexible conductor tubing, said conductor tubing capable of being formed into a bend of less than two-inch radius without collapsing the wall of said flexible tubing and with said tubing having a wall of sufficient thickness and composition so as to prevent collapse when the conductor tubing is empty, this device including:

(a) a length of flexible conductor tubing having a substantially constant configuration;

(b) a length of flexible tubular filter membrane in which the filter is bacteria retentive and sized so that the outer diameter of said tubular filter membrane is smaller than the inner diameter of the conductor tubing and with the conductor tubing enclosing said tubular filter membrane, and between this tubular filter and conductor tubing there is sufficient space for fluid flow, said flexible tubular filter membrane being hydrophilic so as to pass fluid absent the passage of air or gas;

(c) a second filter providing vent means and of hydrophobic material and operatively connected to that space between the flexible tubular filter and the interior of the flexible connector tubing, this second filter and vent means secured in a housing so as to protect this second filter from penetration damage and dislocation, this second filter disposed so that air or gas from said space between the IV conductor and the inner flexible filter is required to pass only through said second hydrophobic filter;

(d) a closure means at one end of the flexible tubular filter membrane and configured and disposed to exclude fluid flow from the tubular conductor tubing to the interior of the flexible tubular filter membrane except through the sidewall portion of said filter membrane;

(e) a closure connector at the other end of this flexible tubular filter membrane, this closure connection providing a fluid flow path from the interior of the flexible tubular filter membrane to external means, and (f) a tubular conductor associated with said connector, with said connector having means providing a tubular connecting portion which is connected tightly to said tubular filter membrane and with said connecting portion being attached so as to inhibit any fluid flow through transverse portions of the filter membrane at said connecting portion.

18. A device as in claim 17 in which the flexible conductor is secured to a molded connector with a passageway therethrough, said connector adapted for releaseable connection to a human waste disposal container, said connector having means for connecting the conductor tubing thereto and this connector having a tubular shoulder portion sized to receive and retain the end and inner diameter of the flexible filter membrane on said tubular shoulder portion of the attached connection, this secured end inhibiting any flow of fluid or air.

19. A device as in claim 18 in which the end of the flexible filter membrane is secured to said tubular portion of the connector by applied heat.

20. A device as in claim 19 in which the local heating of the flexible tubular filter membrane reduces the thickness of the wall of said tubular membrane sufficiently to provide said inhibiting of the flow of air or fluid and the reduction of the thickness of the wall produces a tight fitting of the tubular filter membrane on the tubular shoulder.

21. A device as in claim 20 in which the flexible conductor at its other end is secured to a connector adapted for removable connection to a body catheter.

22. A device as in claim 18 in which the connector is formed with bayonette lugs and the mating connection of the waste disposal collector is formed to provide a releaseable securing of said connector end.

* * * * *